US009651466B2

(12) United States Patent
Brown et al.

(10) Patent No.: US 9,651,466 B2
(45) Date of Patent: May 16, 2017

(54) EDGE SHARPNESS MEASUREMENT

(71) Applicants: Christopher Brown, Worcester, MA (US); Jocelyn Close, Worcester, MA (US); Jason Hopkins, Worcester, MA (US); Michael Dragonas, Worcester, MA (US); Frank Bruton, Worcester, MA (US)

(72) Inventors: Christopher Brown, Worcester, MA (US); Jocelyn Close, Worcester, MA (US); Jason Hopkins, Worcester, MA (US); Michael Dragonas, Worcester, MA (US); Frank Bruton, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 196 days.

(21) Appl. No.: 14/341,168

(22) Filed: Jul. 25, 2014

(65) Prior Publication Data

US 2015/0047423 A1 Feb. 19, 2015

Related U.S. Application Data

(60) Provisional application No. 61/858,373, filed on Jul. 25, 2013.

(51) Int. Cl.
*G01N 3/58* (2006.01)

(52) U.S. Cl.
CPC ..................... *G01N 3/58* (2013.01)

(58) Field of Classification Search
CPC ........................................................ G01N 3/58
See application file for complete search history.

(56) References Cited

U.S. PATENT DOCUMENTS

| 3,921,967 A | * | 11/1975 | Campbell | ............. | A63C 11/08 |
| | | | | | 269/101 |
| 4,850,252 A | * | 7/1989 | Sewell | .................. | A63C 11/06 |
| | | | | | 76/83 |

* cited by examiner

*Primary Examiner* — Erika J Villaluna
(74) *Attorney, Agent, or Firm* — Chapin IP Law, LLC

(57) ABSTRACT

An edge sharpness measurement apparatus includes a clamp for securing a test medium against a frictional member, and an engagement mechanism for a normal force, such that the normal force directs the test medium against the frictional member with a force based on operational conditions of the test medium. A further engagement mechanism is for a tangential force, in which the engagement mechanism is adapted to increase the tangential force to identify a tangential force sufficient to dispose the frictional member across the test medium. A pivot defines an angle of application of the tangential force relative to the normal force, such that disposing the frictional member across the test medium defines a point of overcoming frictional forces between the test medium and the frictional member. A measurement device, such as a gauge or range on a spring, measures the tangential force sufficient to dispose the frictional member.

22 Claims, 3 Drawing Sheets

EDGE SHARPNESS MEASUREMENT

RELATED APPLICATIONS

This patent application claims the benefit under 35 U.S.C. §119(e) of U.S. Provisional Patent App. No. 61/858,373, filed Jul. 25, 2013, entitled "EDGE SHARPNESS MEASUREMENT," incorporated by reference in entirety.

BACKGROUND

Since the inception of hand tools, an edge resulting from tapered sides meeting at a "point" has often been employed for frictional intervention of various materials. Early examples dating back to medieval times include swords, axes, shovels and plows. While it is colloquially known as a "sharp" edge, there has been little formal designation of degrees of "sharpness" for the various devices which employ such a "cutting edge." In conventional approaches, therefore, measuring the quality, or sharpness, of cutting edges has been conducted by simple tests rather than mathematical and scientific methods. To test the sharpness of scissors in a barber shop, for example, the barber generally will moisten the surface of a fingernail then draw it down the length of edge. If the fingernail catches, the blade must be smoothed out. If the nail glides effortlessly down the blade, it is too dull, but if the edge slightly cuts into the nail then the bevel has been set properly. A slightly less crude method is with the use of a string. In this test, the sharpness of the edge is considered a direct correlation to the amount of force necessary for the blade to cut through a loop of thread. Using a loop of thread attached to the small spring scale, the force is measured and a corresponding table is included for how much force is required for a knife blade dependent on its woodworking uses

SUMMARY

An edge sharpness detection or measurement refers to a degree of friction encountered by the edge against a surface, and may therefore apply to a variety of material handling contexts, such as surgical blades, manufacturing dies, industrial saws and other contexts where forced engagement for frictionally engaging and/or severing objects is employed. Industrial uses for cutting materials can be substantial, for example it has been estimated that Boeing Corporation spends $1M per day on cutting materials. An apparatus and method for measuring effectiveness and prolonging effective lifespan of cutting members may be lucrative for maximizing the lifecycle of consumable cutting materials.

Configurations herein are based, in part, on the observation that many mechanical contexts rely on the sharpness of an edge. For example, common cutting tools such as knives and scissors become difficult to operate with a dull edge. In the sports realm, skis, snowboards and skates rely on a sharp edge for predictable performance on a slick surface. Unfortunately, conventional approaches to blade maintenance suffers from the shortcoming that blades are often permitted to wear up until and beyond the point of compromised performance. It can be difficult to accurately and conveniently measure the wear of a blade to determine the point at which edge wear diminishes performance to an unacceptable level. Users of the bladed device therefore acquiesce with lessened performance because they are gradually "conditioned" to the edge wear and/or because it is inconvenient to accurately determine sharpness and identify deterioration. Accordingly, configurations herein substantially overcome the above described shortcomings of blade maintenance by providing a convenient apparatus for measuring blade sharpness without elaborate setup of removing the blade from service for an extended period.

Configurations disclosed herein employ a ski blade as an example application of the disclosed device, however the approach is equally applicable to any bladed device such as snowboards, skates, knives, and other suitable bladed objects which may be engaged by the device. The edge measurement device engages and object under test such as a ski, and clamps around the object to secure the blade. A pivoting frame sets a cutting angle against a frictional member, and a normal force biases the edge against the frictional member at the set angle. An actuator or adjustor such as a screw driven spring applies a tangential force against the frictional member to determine the force required to displace the frictional member against the blade at the defined cutting angle and normal force.

The frictional member may be a surface which is disposed or forced against the test medium at a tangential force for simulating an expected operational force experienced by the blade during deployment. Generally, the bladed object under test may be characterized as having an edge, although planar surface friction may also be evaluated. An edge as employed herein defines a small radius on the object under test that focuses applied force in a focused streamlined manner, and may take the form of a tapered length of a blade. While such an edge or blade may often be referred to as "sharp," a radius is nonetheless exhibited. Angular orientation for directing the tangential force relative to the normal force is based on an angle at the center of this radius.

For example, in the case of a sharpened edge of a downhill ski, the normal force simulates the weight and force applied of the skier, and the tangential force simulates the "slipping" due to friction of the ski edge over the snow when the edge in carved into the snow. To characterize the edge of a ski, the sharpness and edge roundness of ski edges may be considered and simplified to another form of a cutting tool. This simplification can then relate the skis to machining and the cutting forces associated with machining. In previous works, skis have been tested by simulating the machining of ice. By machining the ice at rake angles of −15° to −60°, it has been determined that the cutting force components were approximately independent of cutting speed and that a magnitude of the resultant force increased with a negative rake angle.

In a particular configuration, the frictional member is defined by a cutting blade, and a resistance to sliding is defined by a sharpness of the blade, such that a sharper blade requires a greater tangential force for disposing the frictional member.

In one configuration, the test medium corresponds to a skiing surface and the normal force corresponds to weight of skier, and the tangential force corresponds to sliding engagement of a ski edge over snow. In other arrangements, the cutting edge is a cutting edge of at least one of cutting knives, surgical tools and machining tools. In general, the frictional member has a cutting edge, and the tangential force corresponds to sliding engagement of a cutting edge against cutting material.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 3b shows varying angles of engagement of the ski of FIG. 3a.

DETAILED DESCRIPTION

Disclosed further below is an edge sharpness measurement apparatus and method suitable for use with any rigid edge, including ski edges, knives, surgical tools, or other mechanism or machine for applying a frictional intervention, cutting, or severing force. The measurement apparatus includes a clamp for securing an object under test (test medium) against a frictional member, and an engagement mechanism for applying a normal force, such that the normal force directs the test medium against the frictional member with a force based on operational conditions of the test medium. A further engagement mechanism is for a tangential force, in which the engagement mechanism is adapted to increase the tangential force in response to test parameters and further adapted to identify a tangential force sufficient to dispose the frictional member across the test medium. A pivot defines an angle of application of the tangential force relative to the normal force, such that disposing the frictional member across the test medium defines a point of overcoming frictional forces between the test medium and the frictional member. A measurement device, such as a gauge or range on a spring, measures the tangential force sufficient to dispose the frictional member. Thus, the tangential force is based on coefficient of friction of the test medium and the angle. The angle is based on an edge radius for defining a center of rotation, referring to the relatively small radius defined by a center of the cutting edge.

Configurations discussed below demonstrate an example configuration for illustrating the principles and techniques employed herein for a method and apparatus to measure edge sharpness using the edge sharpness measurement device. The example configuration depicts a ski as the object under test, and tests the sharpness of an edge of the ski. Alternate configurations may apply the depicted approach to any suitable object under test for measuring sharpness.

Figure 1:
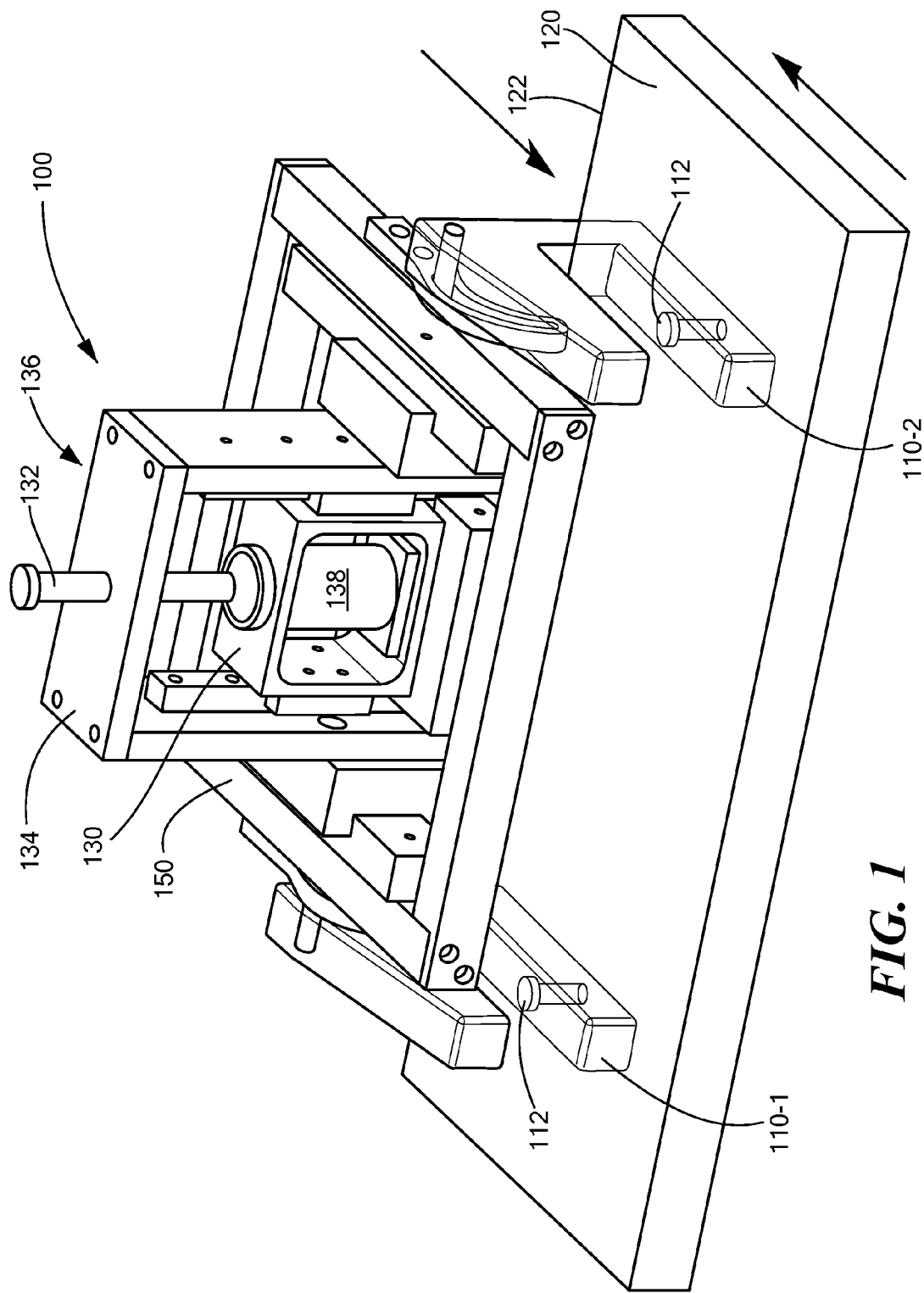
FIG. 1 shows a perspective view of the edge sharpness measurement device.

FIG. 1 shows a perspective view of the edge sharpness measurement device. Referring to FIG. 1, the edge sharpness measurement device 100 (device) includes a plurality of test medium clamps 110-1 . . . 110-2 (110 generally) for securing an object under test 120 for measuring and testing an edge 122 of the object under test 120. The test medium clamps 110 pivotally attach to a frame 150 for angular adjustment around the object under test 120 (test object) The example arrangement depicts a ski as the test object 120. The test medium clamps 110 employ threaded knobs 112 for securing the test object 120. A normal force adjustor 130 employs a threaded shaft 132 for moveable attachment to a body 134. The body 134 attaches to the frame 150 for applying a varying normal force (arrow 136) via a spring 138.

Figure 2:
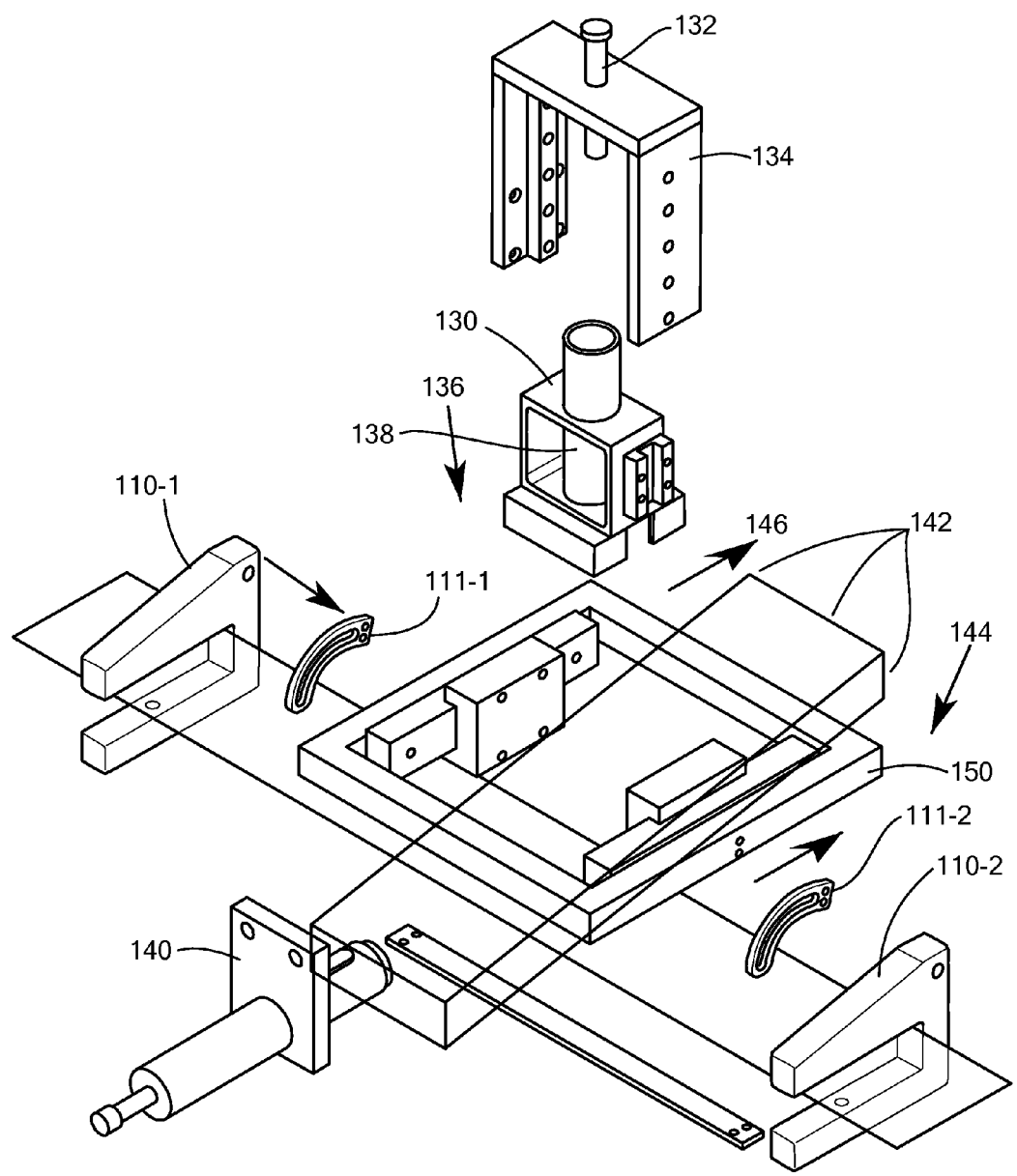
FIG. 2 shows an exploded view of the device of FIG. 1.

FIG. 2 shows an exploded view of the device of FIG. 1. Referring to FIGS. 1 and 2, the edge sharpness measurement device 100, as disclosed herein, therefore includes the normal force adjustor 130 and a tangential force adjustor 140. One or more test medium clamps 110 secure the object under test 120 at an angle 152 (FIG. 3a) against a frictional member comprised of a frictional material 142 based on the normal force 136 applied by the normal force adjustor 130. The tangential force adjustor 140 disposes a frictional material 142 across the edge 122 while the tangential force 136 drives the test object 120 and corresponding edge 122 against the frictional material 142, in the direction shown by arrow 146. The tangential force adjustor 140 experiences a resistance force in response to disposing the frictional material 142 across the edge, shown by arrow 144. The tangential force adjustor 140 has a force measurement mechanism such as a spring, plunger or other approach for measuring the force required to dispose the frictional material 142 across the edge 122 of the test object 120.

Sharpness is measured via a frictional material engagement for securing the frictional material 142 against an edge 122 of an object under test 120 in response to varying tangential force from the tangential force adjustor 140. The frictional material engagement includes a frame 150 for biasing the frictional material against the object under test, in which the frame is disposed between the normal force adjustor 130 and the object under test 120.

Since a resistance imposed by the edge 122 varies at different angles, curved brackets 111-1, 111-2 attach the respective clamps 110 to the frame 150 for securing the test object 120 at a particular angle against the frictional material 142. FIG. 3a shows the device of FIGS. 1 and 2 engaging a ski edge. Referring to FIGS. 1, 2 and 3a, the object under test 120 is a ski, which is secured in the clamps 110 by threaded knobs 112. The clamps 110 are secured to the frame 150 around a pivot point 113 by the curved brackets 111, omitted in FIG. 3a for clarity. The clamps 110 maintain the test object 120 at an angle 152 based on the pivot point 113 and curved brackets 111. The angle 152 affects an aggressiveness of "cut" exerted by the edge 122 on the frictional material 142 at a given normal force 136. The normal force adjustor 130 exerts the normal force 136, as the tangential force adjustor 140 disposes the frictional material 142 across the edge 122.

The normal force adjustor 130 further comprises a compression control configured for varying the normal force 136. In the example arrangement, the compression control includes a compression spring, such that the compression spring is responsive to a threaded shaft for increasing the normal force 136. Alternatively, other suitable means, such as hydraulic, pneumatic or elastic may be employed. Similarly, the tangential force adjustor 140 further comprises a compression member, such that the compression member is secured to the frame 150 and configured for applying a varying force to the frictional material 142 at an angle 152 defined by the test medium clamp 110.

Figure 3B:
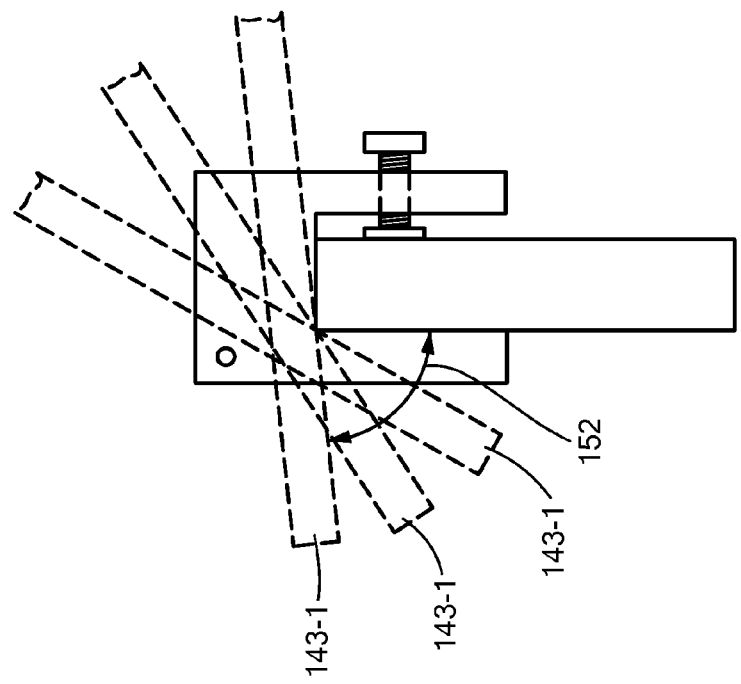
Figure 3A:
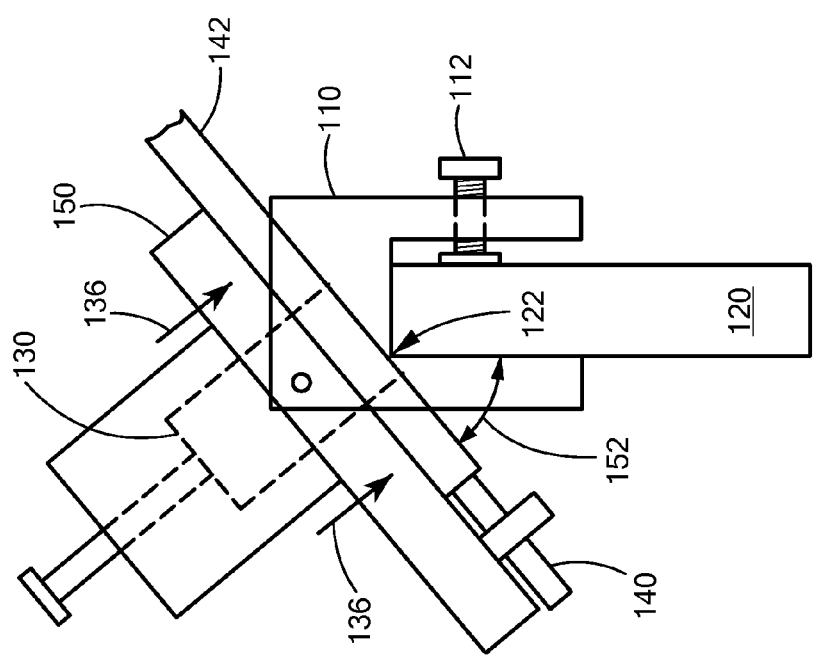
FIG. 3a shows the device of FIGS. 1 and 2 engaging a ski edge.

FIG. 3b shows varying angles of engagement of the ski of FIG. 3a. Depending on the setting of the clamps 110, which may be fixed by any suitable means such as screws, latches, or detents, the frictional material 142 orients at different positions 143-1 . . . 143-3 (143 generally). The position 143, set by angle 152, determines the aggressiveness of cut and whether the edge 122 penetrates and severs material or stops against the frictional material 142.

In deployment of the device, once the device had been manufactured, operation includes testing material into the material holder and securing with set screws. Next, the device is clamped to the ski via the ski clamps 110 and the clamping mechanism. The ski edge 122 is securely fastened up against the back of the clamp such that the material holder is touching the ski edge to be tested. Once this has been completed, the square frame 150 is adjusted to the desired angle using a protractor and locked in place using the clamping mechanism on the ski clamp. Next, the normal force adjustor 130 applies a normal force on the material which is touching the edge 122. Finally, with the proper normal force 136 being applied, a test operator compresses the spring in the tangential direction using the compressor spring in the tangential force adjustor 140. One of two things will happen: either the spring will compress all the way with no movement on the ice, which means that the ski edge is sharp and tuning is not required, or the material will slip on the edge, which indicates that the edge needs to be tuned. For an example frictional material 142, a polyethylene piece was used in the material holder.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. An edge sharpness measurement device, comprising:
    a normal force adjustor;
    a tangential force adjustor;
    a test medium clamp for securing an object under test at an angle against a frictional material based on a normal force applied by the normal force adjustor, the normal force representing a simulated weight and simulated force of a simulated user of the object;
    a frictional material engagement for securing the frictional material against an edge of the object under test in response to varying tangential force from the tangential force adjustor; and
    a measurement device for measuring a tangential force from the tangential force adjustor.

2. The device of claim 1 wherein the frictional material engagement includes a frame for biasing the frictional material against the object under test, the frame disposed between the normal force adjustor and the object under test.

3. The device of claim 2 wherein the normal force adjustor further comprises a compression control, the compression control configured for varying the normal force.

4. The device of claim 3 wherein the compression control includes a compression spring, the compression spring responsive to a threaded shaft for increasing the normal force.

5. The device of claim 4 wherein the tangential force adjustor further comprises a compression member, the compression member secured to the frame and configured for applying a varying force to the frictional material at an angle defined by the test medium clamp.

6. The device of claim 1 wherein the tangential force is perpendicular to the edge on an elongated dimension of the object under test.

7. The device of claim 1 wherein compression member is configured to dispose the tangential force adjustor to drive a tangential point of the edge against the frictional material, the tangential point defined by a meeting of two sides of the object under test.

8. A method for measuring edge sharpness, comprising:
    engaging an edge of an object under test against a frictional material by applying a force normal to the edge, the force normal to the edge representing a simulated weight and simulated force of a simulated user of the object under test;
    applying a tangential force to the engaged frictional material for disposing the frictional material against the object under test; and
    measuring the applied tangential force at an angle of engagement defined by the orientation of the object under test to the frictional material with a measurement device.

9. The method of claim 8 further comprising biasing the frictional material at an angle against the object under test, the frame disposed between the normal force adjustor and the object under test.

10. The method of claim 9 further comprising applying the normal force from a compression spring, the compression spring responsive to a threaded shaft for increasing the normal force.

11. The method of claim 10 further comprising varying the angle for determining an angle at which a tangential force disposes the frictional material against the edge.

12. The method of claim 8 further comprising securing the object under test in a clamp, the clamp adapted for angular adjustment relative to a frame for securing the edge against the frictional material at the adjusted angle.

13. A sharpness measurement apparatus comprising:
    a clamp for securing a test medium against a frictional member;
    an engagement mechanism for a normal force, the normal force directing the test medium against the frictional member with a force based on operational conditions of the test medium, the normal force representing a simulated weight and simulated force of a simulated user of the test medium; and
    an engagement mechanism for a tangential force, the tangential force engagement mechanism adapted to force the frictional member across the test medium and to increase the tangential force in response to test parameters and further adapted to identify a tangential force sufficient to dispose the frictional member across the test medium;
    a pivot for defining an angle of application of the tangential force relative to the normal force; and
    a measurement device for measuring a tangential force.

14. The apparatus of claim 13 wherein disposing the frictional member across the test medium includes overcoming frictional forces between the test medium and the frictional member resulting from disposing the frictional member across the test medium.

15. The apparatus of claim 13 wherein the angle is based on an edge radius for defining a center of rotation.

16. The apparatus of claim 13 wherein the test medium is defined by a cutting blade, and a resistance to sliding is defined by a sharpness of the blade, such that a sharper blade requires a greater tangential force for forcing against the frictional member.

17. The apparatus of claim 13 further comprising a measurement device for measuring the tangential force from the tangential force engagement mechanism sufficient to force the frictional member across the test medium.

18. The apparatus of claim 17 wherein the tangential force is based on coefficient of friction of the test medium and the angle.

19. The apparatus of claim 13 wherein the frictional member corresponds to a skiing surface and the normal force corresponds to weight of skier.

20. The apparatus of claim 19 wherein the tangential force corresponds to sliding engagement of a ski edge over snow.

21. The apparatus of claim 13 wherein the test medium has a cutting edge, and the tangential force corresponds to sliding engagement of a cutting edge against cutting material.

22. The apparatus of claim 13 wherein the cutting edge is a cutting edge of at least one of cutting knives, surgical tools and machining tools.

* * * * *